US010940284B2

(12) United States Patent
Buechi

(10) Patent No.: US 10,940,284 B2
(45) Date of Patent: *Mar. 9, 2021

(54) BREATHING TUBE

(71) Applicant: HAMILTON Medical AG, Bonaduz (CH)

(72) Inventor: Rudolf Buechi, Chur (CH)

(73) Assignee: Hamilton Medical AG

( * ) Notice: Subject to any disclaimer, the term of this patent is extended or adjusted under 35 U.S.C. 154(b) by 224 days.

This patent is subject to a terminal disclaimer.

(21) Appl. No.: 16/120,888

(22) Filed: Sep. 4, 2018

(65) Prior Publication Data

US 2018/0369533 A1 Dec. 27, 2018

Related U.S. Application Data

(63) Continuation of application No. 14/382,547, filed as application No. PCT/EP2012/069147 on Sep. 27, 2012, now Pat. No. 10,105,510.

(30) Foreign Application Priority Data

Mar. 2, 2012 (DE) .................. 10 2012 101 795

(51) Int. Cl.
*A61M 16/10* (2006.01)
*A61M 16/08* (2006.01)
(Continued)

(52) U.S. Cl.
CPC .... *A61M 16/1065* (2014.02); *A61M 16/0003* (2014.02); *A61M 16/0816* (2013.01);
(Continued)

(58) Field of Classification Search
CPC .......... A61M 16/1065; A61M 16/0003; A61M 16/1075; A61M 16/16; A61M 16/0875;
(Continued)

(56) References Cited

U.S. PATENT DOCUMENTS 3,556,097 A * 1/1971 Wallace .............. A61M 16/104
128/202.23
4,306,743 A 12/1981 Hinshaw
(Continued)

FOREIGN PATENT DOCUMENTS

DE 4438216 A1 5/1995
DE 4441380 A1 5/1995
(Continued)

*Primary Examiner* — Kendra D Carter
*Assistant Examiner* — Victoria Murphy
(74) *Attorney, Agent, or Firm* — Jansson Munger McKinley & Kirby Ltd.

(57) ABSTRACT

A breathing tube for a patient ventilator system providing humidified breathable gas is provided, the tube including inhalation and exhalation pathways formed in part by inhalation and exhalation tubes. A coupler member is attached at one end to the exhalation tube and forms part of the exhalation pathway, the coupler member has an integrated coupler-member electrical heating device electrically connected to the tube-portion electrical heating device. A connecting piece is detachably attachable to the other end of the coupler member and forms a part of the exhalation pathway, the connecting piece and coupler member together forming a hollow space therewithin extending from within the connecting piece to within the coupler member. A filter element is within the hollow space and extends from within the connecting piece into the coupler member, the coupler-member heating device is along the hollow space, surrounding the filter element, and adapted to heat the filter element.

11 Claims, 2 Drawing Sheets

(51) Int. Cl.
*A61M 16/00* (2006.01)
*A61M 16/16* (2006.01)

(52) U.S. Cl.
CPC .... *A61M 16/0875* (2013.01); *A61M 16/1075* (2013.01); *A61M 16/1095* (2014.02); *A61M 16/0093* (2014.02); *A61M 16/0883* (2014.02); *A61M 16/1055* (2013.01); *A61M 16/16* (2013.01); *A61M 2205/14* (2013.01); *A61M 2205/3368* (2013.01); *A61M 2205/36* (2013.01); *A61M 2205/3653* (2013.01); *A61M 2205/75* (2013.01); *A61M 2205/7563* (2013.01)

(58) Field of Classification Search
CPC .......... A61M 16/0816; A61M 2205/75; A61M 2205/36; A61M 16/1095; A61M 2205/3368; A61M 2205/3653; A61M 16/0093; A61M 2205/7563; A61M 16/1055; A61M 16/107; A61M 16/106; A61M 16/105

See application file for complete search history.

(56) References Cited

U.S. PATENT DOCUMENTS

| | | | |
|---|---|---|---|
| 4,727,871 A | * | 3/1988 | Smargiassi ........ A61M 16/0087 128/204.17 |
| 5,600,752 A | | 2/1997 | Lopatinsky |
| 7,120,354 B2 | * | 10/2006 | MacKie ................ A61M 16/08 392/480 |
| 7,497,215 B1 | | 3/2009 | Nguyen et al. |
| 2006/0096597 A1 | | 5/2006 | Amann |
| 2008/0105257 A1 | | 5/2008 | Klasek et al. |
| 2010/0319699 A1 | | 12/2010 | Wood |

FOREIGN PATENT DOCUMENTS

| | | | | |
|---|---|---|---|---|
| DE | 60310062 T2 | 6/2007 | | |
| DE | 102007003455 A1 | 8/2008 | | |
| DE | 102008039137 B3 | 2/2010 | | |
| EP | 0672430 A2 | 9/1995 | | |
| EP | 1222940 A2 | 7/2002 | | |
| EP | 2229973 A2 | 9/2010 | | |
| EP | 2269680 A1 | 1/2011 | | |
| GB | 1294307 A | 10/1972 | | |
| GB | 2277689 A | * | 11/1994 | ........ A61M 16/1075 |
| GB | 2277689 A | 11/1994 | | |
| JP | 2000-500359 | 1/2000 | | |
| JP | 2005-261858 | 9/2005 | | |
| WO | 97/018001 | 5/1997 | | |
| WO | 2010073161 A1 | 7/2010 | | |

* cited by examiner

BREATHING TUBE

RELATED APPLICATIONS

This application is a continuation of U.S. Ser. No. 14/382,547, filed Sep. 2, 2014, which was a national-phase entry under 35 USC § 371 of International Application No. PCT/EP2012/069147, filed on Sep. 27, 2012, which claims priority to German Patent Application No. DE 10 2012 101 795.6, filed on Mar. 2, 2012. The entire disclosure and contents of these applications are incorporated by reference into the present application.

FIELD OF INVENTION

The present invention pertains to a breathing tube for conducting a gas mixture in a respirator for ventilating patients and to a breathing tube system.

BACKGROUND OF THE INVENTION

When patients are being ventilated mechanically on an intensive-care ward, for example, the patient to be ventilated is connected pneumatically to the ventilator by means of a breathing tube system. Because the breathing gas which is supplied to the patient must be adjusted with respect to temperature and humidity to the physiological needs of the patient, a respiratory humidifier is arranged in the inhalation or inspiration tube to warm and humidify the breathing gas. The respiratory humidifier comprises a liquid container filled with distilled water in the usual manner; the inhalation gas is conducted through this container, and its moisture content is thus increased.

To prevent moisture from condensing inside the breathing tube system, the inhalation tube and the expiration or exhalation tube are usually provided with electrical tube heaters, which warm the inhalation and exhalation gas flowing through them during operation. A loop of heating wire, for example, is used, which is integrated into the interior of the inhalation or exhalation tube, or the inhalation or exhalation tube is wrapped in each case with a coil of heating wire.

Breathing tube systems of this type are known from, for example, DE 10 2008 039 137 B3, DE 10 2007 003 455 A1, and DE 44 41 380 A1.

In the exhalation part of the breathing tube system, it is possible, especially in the case of patients with infectious diseases, to install filters to prevent the exhalation gas from carrying pathogens into the environment, which could result in additional patients or medical staff becoming infected. A filter of this type must be designed so that no condensate can form in it, because this would clog the filter and thus impair the filtering function. In the worst case, the ventilation function can also become defective, which can lead to negative results for the patient. Normally, the formation of condensate in the filter is prevented by means of additional heating devices and/or by means of water traps, as disclosed, for example, in U.S. Pat. No. 4,727,871. The general use of filter elements in ventilators is disclosed, for example, in U.S. Pat. No. 3,556,097.

GB 1 294 307 A describes a heatable anesthesia filter, which is used on the inhalation side of a respirator. A sleeve, in which a heater is integrated, is placed over a hermetically sealed container which contains a filter. The container is connected to the inhalation tubes by means of connecting pieces, one arranged at the beginning and the other at the end of the container.

The disadvantage of the above-mentioned breathing tube systems according to the prior art is that the heating of filters requires additional components such as cables, connectors, etc., which, because of the large number of cables and tubes to be connected, can lead to a loss of time and to the possible confusion of the operators. It can also be bothersome in the patient environment and can be susceptible to damage. The alternative use of unheated filters carries with it the danger of clogging attributable to the formation of condensate as previously described.

SUMMARY OF THE INVENTION

It is therefore the object of the present invention to provide a breathing tube which makes it possible to filter the exhalation gas effectively, reliably and permanently, avoids the formation of water condensate in the filter, and minimizes the number of additional elements such as tubes, electrical lines, and their connections, etc.

This object is achieved by the present invention. Advantageous elaborations and embodiments are the subjects of the subclaims.

According to the invention, a breathing tube for conducting a gas mixture in a ventilation system is provided with a tube portion; a coupler connectable to the tube portion; a connecting piece connectable to the coupler and which is attachable to a tube or a machine, wherein a filter element for filtering the gas mixture is arranged between the coupler and the connecting piece. The coupler includes a first integral electrical heating device which surrounds the filter element and is adapted to heat the filter element effectively. As a result of the transfer of heat by convection or conduction from the coupler to the filter element, it is ensured that, when the gas mixture is being filtered, no condensate which could clog the filter element or the filter will form. In addition, the ventilation tube is simple and space-saving in design, and performs its task without any additional elements besides the connecting piece.

It is especially advantageous for the filter element and the connecting piece to form a single integral unit. As a result, the ventilation tube is simplified even more, because fewer components are needed.

The tube portion, the coupler, and the connecting piece preferably have a circular cross-section. This allows the use of standard commercial cylindrical filter elements. Handling is also simplified as are assembly and possible disassembly of the individual elements.

It is also advantageous to form the connection between the coupler and the connecting piece in detachable fashion as a screw-in or plug-in connection or as a bayonet mount. These types of connections are easy to attach and release, which facilitates handling, and their use is not unusual in the clinical field.

In order to be able to use the breathing tube in current ventilators already present in hospitals, it is advantageous for the tube to be configured as a medical-grade single-use/disposable article.

The tube portion preferably includes a second electrical heating device which is connectable to the first electrical heating device. It is also advantageous for at least certain parts of the first and/or the second electrical heating device to be configured as heating coils. Here the second electrical heating device is preferably integrated into the walls of the tube portion. A heating coil represents a simple design and ensures effective heating of the ventilation tube and thus effective transfer of heat to the gas mixture in the ventilation tube. The first and second electrical heating devices can be connected to each other by means of simple plug-in connectors, which are sturdy and inexpensive.

It is also advantageous for the tube portion and the coupler to be configured as a single, integral unit. This, too, results in an especially simple design, producible, for example, by means of coextrusion of the components. The fewer the number of elements of the ventilation tube or of the entire breathing tube system, the less effort is required of the operators for assembly, etc.

The way in which the coupler and filter element are arranged guarantees maximum heat transfer from the first electrical heating device to the filter element. The heat transfer occurs here by convection, for example, or also by conduction. It must be kept in mind that the filter function of the filter element may not be impaired; that is, the gas mixture must be able to flow through the filter at the desired rate so as not to interfere with the ventilating function.

The filter element is preferably cylindrically shaped, wherein the distance between the outer lateral surface of the filter and the inner lateral surface of the coupler is from approximately 0.1 mm to approximately 8 mm. These types of cylindrical filters are industrially produced and commercially obtainable. An example of the principle of a design of a filter of this type without a heater is shown in FIGS. 11-13 of U.S. Pat. No. 3,356,097. Here, a ring-shaped filter is arranged axially inside a housing, and the breathing gas flows from the outer lateral surface of the ring through the filter material to the inner lateral surface and from there through the outlet opening of the housing. It is obvious, however, that various other designs of filter elements with connecting pieces and couplers can also be used in the present invention. For example, an essentially spherical filter element is conceivable, which would comprise a hollow space into which the gas mixture would flow from the outer surface into the filter material.

It is also advantageous for the breathing tube to include a sensor for detecting parameters of the connection between the coupler and the connecting piece. Thus it is possible, by way of the user interface of a respiratory humidifier, for example, or the interface on the ventilator, to activate a display which confirms that the coupler and the connecting piece have been properly connected. Thus, the function of the filter element can be monitored more effectively, and an incorrect attachment and other malfunctions can be detected more quickly.

It is especially advantageous for the connecting piece to include its own electrical heating device which is electrically connectable to the heating device of the coupler. As a result, the heat output for the filter element can be increased, wherein the electrical connection between the coupler and the connecting piece can be established easily, for example, by way of the elements used to attach them. Thus, the above-mentioned function of a sensor can also be realized, in which, for example, the presence of an effective electrical connection between the coupler and the connecting piece confirms that the connection has been properly established. Alternatively, the heating device of the connecting piece and possibly that of the coupler can also be supplied by way of a connecting element which is connected directly to the connecting piece.

Also according to the invention is a breathing tube system with an inhalation tube and an exhalation tube which is formed as a ventilation tube as described above.

BRIEF DESCRIPTION OF THE DRAWINGS

The invention is explained below on the basis of exemplary embodiments with reference to the attached figures, in which.

DETAILED DESCRIPTION

Figure 1:
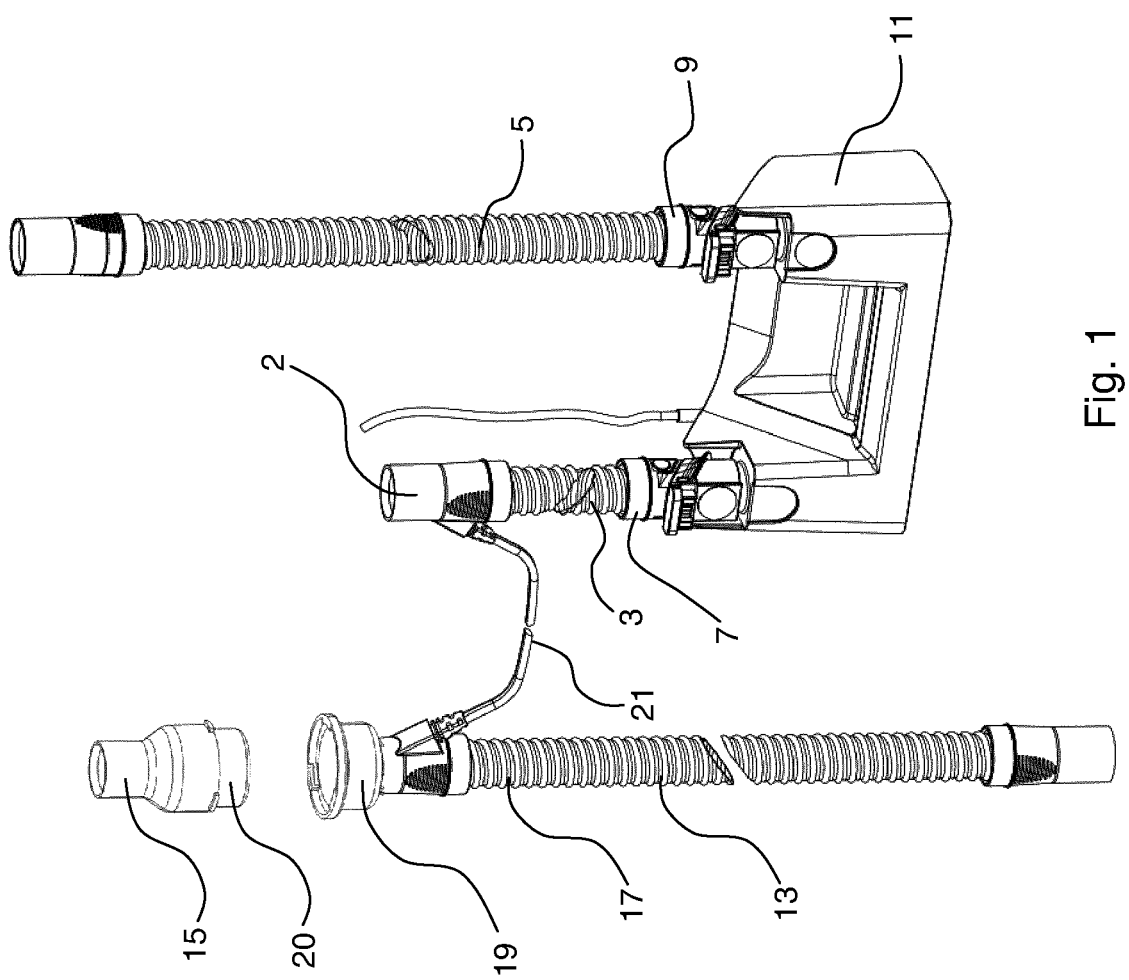
FIG. 1 is a schematic diagram of a preferred embodiment of the breathing tube system of the present invention.

FIG. 1 shows a perspective diagram of the inventive breathing tube system. A ventilator (not shown in FIG. 1) is connected to a first inhalation tube 3 by a first connecting element. First inhalation tube 3 and a second inhalation tube 5 are connected to a liquid container 11 of a respiratory humidifier (not shown in FIG. 1) by appropriate connecting pieces 7 and 9, respectively. The free end of second inhalation tube 5 can be connected to a Y-piece (not shown) which establishes the connection to the patient by way of a mouthpiece. First and second inhalation tubes 3 and 5 are both equipped with electrical tube heaters in the form of heating coils integrated into the tube walls. In FIG. 1, only the pneumatic connections between first and second inhalation tubes 3 and 5 and the liquid container 11 via connecting pieces 7 and 9, respectively, are shown; the electrical connection of all of the electrical lines passing through the tubes is accomplished by contact elements which are integrated into connecting pieces 7 and 9 and which establish the electrical connection by contacting corresponding opposing contact elements on the housing of the breathing air humidifier. An exhalation tube 13 can be connected to the ventilator by means of a connecting piece 15. The other end of exhalation tube 13 is connected during operation to the Y-piece near the patient.

In the embodiment shown here, exhalation tube 13 embodies the breathing tube according to the invention and comprises a tube portion 17 which is provided with an electrical heating device 24 (also referred to herein as "first electrical heating device") configured as a heating coil integrated into the tube wall. Between connecting piece 15 and tube portion 17, exhalation tube 13 includes a coupler 19 with a filter element 20, wherein coupler 19 is permanently connected to tube portion 17 but detachably connected to connecting piece 15. The details of the exhalation tube will now be described with reference to FIG. 2.

Figure 2:
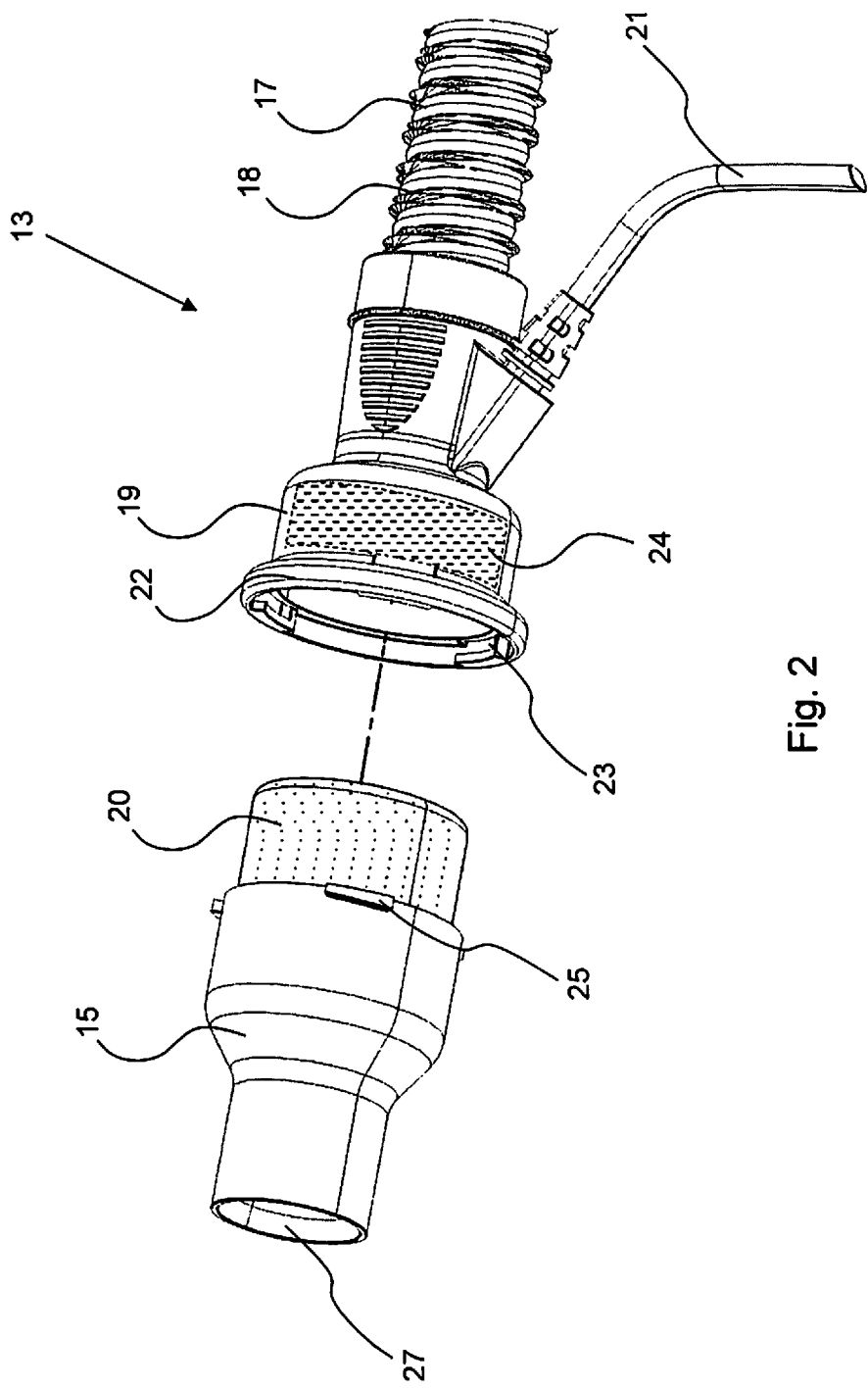
FIG. 2 is a perspective diagram of a preferred embodiment of the ventilation tube according to the present invention.

In the embodiment shown in FIG. 2, a connecting element 21 is arranged between the connecting piece 2 of first inhalation tube 3 and coupler 19 of exhalation tube 13 to establish the electrical connection. In addition to the pneumatic opening, connecting piece 2 of first inhalation tube 3 includes a sleeve element into which a corresponding plug element at the end of connecting element 21 is permanently plugged. In the same way, coupler 19 of exhalation tube 13 also comprises a sleeve element into which corresponding plug element of connecting element 21 is permanently plugged. The term "permanently" in this context is to be understood as meaning that operators cannot disconnect the electrical connections between connecting element 21 and connecting piece 2 or coupler 19 by a reasonable amount of effort.

Because the diagram in FIG. 1 pertains to the elements which form, as usual, the medical-grade single-use/disposable articles representing the necessary replaceable accessories for the function of a respiratory humidifier together with the breathing tube system, other elements such as the Y-piece or the housing of the respiratory humidifier have been omitted.

The material of the tubes, that is, of first inhalation tube 3, second inhalation tube 5, and exhalation tube 13, is of a suitable plastic material such as polyethylene or polypropylene. Other suitable materials may also be used. The tubes are extruded or coextruded by known technology. The inside diameter of the tubes is usually about 19 mm or about 22 mm in the case of a ventilation system for adults, but it would also be possible to use smaller diameters such as 12 mm or 15 mm in the case of ventilation systems intended, for example, for pediatric or infant-care wards. The connecting pieces, which form the transition between the tubes and the corresponding machines or the Y-piece, are also extruded of plastic material. Because strict requirements are imposed on materials in the medical field, these materials must meet the requirements of ISO standard 5367-2000. As previously mentioned, the breathing tube system according to the invention is configured either as a medical-grade, single-use/disposable article or alternatively as a reusable medical article, which can be restored to a usable state by washing and autoclaving. All components of the breathing tube system must also be configured so that they contain no harmful substances and can withstand a cold disinfectant such as CIDEX, Sekusept, Korsolex, etc.

FIG. 2 shows in perspective view the details of exhalation tube 13 of the preferred embodiment of the breathing tube of the present invention. Tube portion 17 includes an electrical heating device 24 configured as a heating coil 18, which is integrated into the tube wall. Cylindrical coupler 19 is connected to tube portion 17, wherein the heating coil 18 is electrically connected to electrical heating device 24 which is integrated into the coupler 19 but which is not visible from the outside. When heating coil 18 of tube portion 17 is carrying heating current, the current also flows through the heating device of coupler 19. Alternatively, it is also conceivable that the heating device of coupler 19 could have its own separate electrical connection and be controlled by way of connecting element 21, which is mounted laterally on coupler 19 by way of a sleeve element. In the embodiment shown in FIG. 2, coupler 19 includes a flange 22 which has a plurality of locking elements 23 on its inside surface. Coupler 19 includes a cylindrical hollow space to receive the filter element 20.

Connecting piece 15 has the shape of a cylinder on the coupler side with essentially the same cross-sectional dimension as coupler 19 and is thus connectable to coupler 19. On the lateral surface of connecting piece 15, locking elements 25 in the form of external projections are arranged, which are adapted to engage with the locking elements 23 of coupler 19 in the manner of a bayonet mount. Alternatively, it would also be possible to use some other type of detachable attachment mechanism such as a screw joint, a magnetic closure, a plug-in connection, or other type of connection familiar to the person skilled in the art.

Proceeding from the part with the larger cross-section, i.e., at the end facing away from connection to coupler 19, connecting piece 15 tapers down in a funnel-like manner to a cylindrical section 27 of smaller cross-section which is adapted to be attached to the appropriately configured opposing piece of a ventilator. Connecting piece 15 also comprises a hollow cylindrical space, in which filter element 20 is accommodated. To hold filter element 20 firmly in position inside the hollow space, retaining elements can be provided, but they may not completely prevent the flow of the gas mixture during operation, that is, during the time that connecting piece 15 and coupler 19 are properly connected to each other. In other words, the installation of filter element 20 between coupler 19 and connecting piece 15 must ensure both sufficient heat transfer from heating device 24 of coupler 19 and sufficient gas mixture flow through the ventilation tube.

For this reason, various configurations within coupler 19 and connecting piece 15 are also possible which deviate from the embodiment shown in FIG. 2 but which still fulfill the function described above.

It is also conceivable that connecting piece 15 could be provided with its own heating device capable of heating filter element 20. This can be achieved, for example, by integrating an electrical heating coil into the lateral surface of connecting piece 15, which coil, in the embodiment illustrated here, can be electrically connected to the heating device in the coupler via the elements of the bayonet mount. As a result, an electrical connection is established between heating device 24 of coupler 19 and the heating device of connecting piece 15. Other types of heating devices are also possible.

It is possible, furthermore, to mount connecting element 21 on connecting piece 15 instead of on coupler 19. The two heating devices can then be supplied with current via the alternative of connecting element 21.

With the subject matter of the present invention, a breathing tube has been provided which makes it possible to filter the exhalation gas effectively, reliably and permanently, avoids the formation of condensate in the filter, and minimizes the number of additional elements such as tubes, electrical lines, and their connections, etc.

The invention claimed is:

1. A breathing tube apparatus for a patient ventilator system providing humidified breathable gas, the apparatus including (a) inhalation and exhalation pathways formed in part by inhalation and exhalation tubes, respectively, and (b) a filter element, the breathing tube apparatus comprising:
   the exhalation tube having a tube-portion electrical heating device therealong;
   a coupler member attached at one of its ends to the exhalation tube and forming a part of the exhalation pathway, the coupler member having an integrated coupler member electrical heating device electrically connected to the tube-portion electrical heating device;
   a connecting piece detachably attachable to another end of the coupler member and forming a part of the exhalation pathway, the connecting piece and coupler member together forming a hollow space therewithin extending from within the connecting piece to within the coupler member; and
   the filter element within the hollow space and extending from within the connecting piece into the coupler member, the integrated coupler member electrical heating device being along the hollow space, surrounding the filter element, and adapted to heat the filter element, thereby avoiding condensate accumulation in the filter element which would interfere with filtering of exhaled gas.

2. The breathing tube apparatus of claim 1 wherein the filter element is secured to the connecting piece.

3. The breathing tube apparatus of claim 1 wherein the exhalation tube, the coupler member, and the connecting piece are each of circular cross-section.

4. The breathing tube apparatus of claim 1 wherein a detachable connection between the coupler member and the connecting piece is a bayonet-mount connection.

5. The breathing tube apparatus of claim 1 configured as a medical single-use/disposable article.

6. The breathing tube apparatus of claim 1 wherein the exhalation tube is permanently attached to the coupler member.

7. The breathing tube apparatus of claim 1 wherein the coupler member and the filter element are configured and arranged to facilitate heat transfer from the coupler-member electrical heating device to the filter element.

8. The breathing tube apparatus of claim 7 wherein the filter element is cylindrical and a distance between an outer lateral surface of the filter element and an inner lateral surface of the coupler member is about 0.1-0.8 mm.

9. The breathing tube apparatus of claim 1 further including a sensor for detecting parameters of a connection between the coupler member and the connecting piece.

10. The breathing tube apparatus of claim 1 wherein the connecting piece includes another electrical heating device electrically connectable to the integrated coupler member electrical heating device.

11. The breathing tube apparatus of claim 1 wherein the exhalation tube, the coupler member and connecting piece form the exhalation path.

\* \* \* \* \*